(12) United States Patent
Badwan (10) Patent No.: US 7,084,144 B2
(45) Date of Patent: Aug. 1, 2006

(54) SULFONYL GROUP CONTAINING COMPOUNDS AND THEIR USE FOR THE TREATMENT OF ERECTILE DYSFUNCTION

(75) Inventor: Adnan Badwan, Amman (JO)

(73) Assignee: The Jordanian Pharmaceutical MFG & Medical Equipment CO LTD, Jo-Naor (JO)

( * ) Notice: Subject to any disclaimer, the term of this patent is extended or adjusted under 35 U.S.C. 154(b) by 0 days.

(21) Appl. No.: 10/848,536

(22) Filed: May 19, 2004

(65) Prior Publication Data

US 2005/0080088 A1    Apr. 14, 2005

Related U.S. Application Data

(63) Continuation of application No. 10/015,591, filed on Dec. 17, 2001, now abandoned.

(60) Provisional application No. 60/257,157, filed on Dec. 22, 2000.

(30) Foreign Application Priority Data

Dec. 22, 2000    (SE)    ..................................... 0004780

(51) Int. Cl.
A61K 31/496    (2006.01)
C07D 405/12    (2006.01)

(52) U.S. Cl. .............................. 514/254.11; 514/252.2; 514/252.12; 514/254.02; 514/254.1; 514/256; 514/317; 514/321; 514/323; 514/326; 514/329; 514/330; 514/331; 544/295; 544/376; 544/377; 544/335; 544/382; 544/383; 544/368; 544/379; 546/196; 546/197; 546/209; 546/214; 546/223; 546/225; 546/236

(58) Field of Classification Search ................ 544/376, 544/377, 295; 514/254.11, 252.2
See application file for complete search history.

(56) References Cited

U.S. PATENT DOCUMENTS

| | | | |
|---|---|---|---|
| 2,507,408 A | 5/1950 | Jacob | |
| 4,431,813 A | 2/1984 | Handte et al. | |
| 6,054,475 A | 4/2000 | Martin et al. | |

FOREIGN PATENT DOCUMENTS

| | | |
|---|---|---|
| DE | 19825182 | 12/1999 |
| EP | 0 021 592 | 1/1981 |
| EP | 0 304 330 | 2/1989 |

(Continued)

OTHER PUBLICATIONS

A Screening Concept Based on a Hypothesis Led to the Development of a Putative Cognitive Enhancer That Stimulates Penile Erection, Jpn. J. Pharmacol. 64, 147-153 (1994), Maeda et al.

(Continued)

*Primary Examiner*—Emily Bernhardt
(74) *Attorney, Agent, or Firm*—Finnegan, Henderson, Farabow, Garrett & Dunner, L.L.P.

(57) ABSTRACT

A compound having the general formula (I):

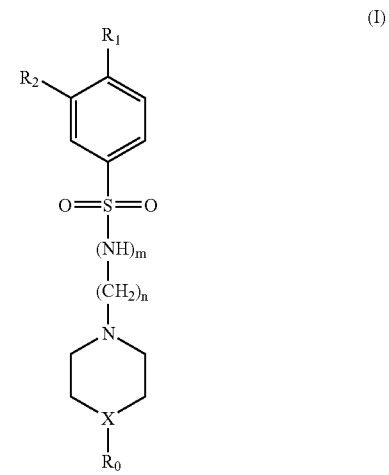

(I)

wherein: X is N or C; $R_0$ is H, a lower alkyl group, a lower O-alkyl group,

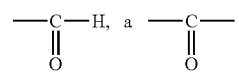

lower alkyl group, a benzyl group, a phenyl group, a heterocyclic amine group, a cycloalkyl group, a cycloalkyl group substituted with O-alkyl or, a furyl group; $R_1$ and $R_2$ are, independently, H, an amine group, a lower alkyl group, a lower O-alkyl group, a lower S-alkyl group or a lower N-alkyl group, or $R_1$ and $R_2$ taken together with the carbon atoms to which they are attached form a five-membered carbocyclic or heterocyclic ring, where the heteroatoms of the heterocyclic ring are one or two oxygen atoms, and/or where any substituent on said carbocyclic or heterocyclic ring is chosen from O, S and N; n is 0,1,2,3 or 4; m is 0 or 1; and pharmaceutically acceptable salts thereof; with the proviso that said compound is not 1-[(4-methoxyphenyl)sulfonyl]piperazine or 1-(1,3-benzodioxol-5-ylsulfonyl)piperazine. The compounds are useful as active ingredients in pharmaceutical compositions and as a medicament for the treatment of erectile dysfunction.

6 Claims, 2 Drawing Sheets

FOREIGN PATENT DOCUMENTS

| | | |
|---|---|---|
| EP | 0 463 756 | 1/1992 |
| EP | 0638 564 | 2/1994 |
| EP | 0 661 266 | 7/1995 |
| EP | 0 702 555 | 3/1996 |
| EP | 0 330 065 | 8/1999 |
| EP | 1 057 829 | 12/2000 |
| WO | WO 94/28902 | 12/1994 |
| WO | WO 95/04049 | 2/1995 |
| WO | WO 98/49166 | 11/1998 |
| WO | WO 98/54164 | 12/1998 |
| WO | WO 99/06367 | 2/1999 |
| WO | WO 99/26616 | 6/1999 |

OTHER PUBLICATIONS

"Design and Synthesis of Potent and Selective 5,6-Fused Heterocyclic Thrombin Inhibitors," Celia Dominguez et al., Bioorganic & Medicinal Chemistry Letters, vol. 9 (1999) 925-930, Dominguez et al.

Fig. 1

Fig. 2

SULFONYL GROUP CONTAINING COMPOUNDS AND THEIR USE FOR THE TREATMENT OF ERECTILE DYSFUNCTION

CROSS REFERENCE TO RELATED APPLICATIONS

This application is a continuation of U.S. application Ser. No. 10/015,591 filed Dec. 17, 2001 now abandoned and claims the benefit of U.S. Provisional Application No. 60/257,157, filed Dec. 22, 2000, the contents of both of which are incorporated herein by reference.

TECHNICAL FIELD OF THE INVENTION

The present invention relates to novel compounds, pharmaceutical compositions containing the same as well as the use of said compounds as a medicament and for the manufacture of a medicament for the treatment of erectile dysfunction.

BACKGROUND ART

Erectile dysfunction is a common disorder among male individuals worldwide. The introduction of sildenafil (the active ingredient in Viagra®) on the market in order to help patients with erectile problems has improved the possibilities to treat such disorders. Sildenafil and compounds closely related thereto are disclosed in EP 463 756, EP 702 555 and WO 98/49166 (all to Pfizer Ltd.). Other compounds useful as active ingredients in medicaments for the treatment of erectile dysfunction are disclosed in EP application no. 99850097.0.

Sexual stimulation leads to nitric oxide (NO) release from the nerve endings and endothelial cells in the spongy erectile tissue, known as corpus carvenosum, of the penis. NO switches on the enzyme guanylate cyclase, which converts guanosine triphosphate (GTP) into cyclic guanosine monophosphate (cGMP). cGMP is a key second messenger vasodilator, which relaxes the vascular smooth muscle of the blood vessels of the corpus carvenosum, leading to a stronger blood flow and an erection. Thus, the presence of cGMP is the main promoter of erection since it prolongs the strong and rich blood flow in the corpus carvenosum, thus prolonging the erection. Cyclic nucleotides are degraded by a group of enzymes known collectively as phosphodiesterases (PDEs). They are a group of ten structurally closely related isoenzymes. Some of these isoenzymes are more specific to certain cyclic nucleotides than to others and they vary in their specificity and affinity. PDE type 5 (PDE5) is very specific for cGMP and has a main function in the corpus carvenosum and is thus a main factor in the erection process. Other isoenzymes exert their physiological actions by acting more specifically on other nucleotides such as cAMP.

Several PDE isoenzymes have been described being expressed and co-expressed in different tissues with many physiological effects. Many PDE inhibitors are not very specific, thus inhibiting a range of more than one PDE at the same time, which could cause a wide contraindication and toxic effects. PDE6 being widely expressed in the rods of the retina is a cyclic AMP (cAMP) specific PDE. cAMP is inhibited by other PDE inhibitors as well, including non-specific PDE5 inhibitors, especially at high concentration.

PDE5 is a cyclic GMP specific PDE with very low or negligible effect on cAMP, with $k_1 >>> k_2$, cAMP $\xrightarrow{K_2}$ 5'-AMP cAMP $\xrightarrow{K_1}$ 5'-GMP while other PDEs (including PDE6, PDE4, and PDE3) have higher affinity for cAMP. Some PDEs such as PDE10 hydrolyze both cAMP and cGMP effectively. In order to stop or seriously reduce cGMP breakdown by PDE5, selective inhibitors of PDE5 are proving to be an effective treatment for erectile dysfunction. These inhibitors selectively inhibit PDE5 by competitively binding with PDE5 active sites. This prevents the hydrolysis of cGMP to the inactive form 5'-GMP, allowing cGMP to accumulate and prolong the vasodilatation effect.

Thus, there is a need for specific PDE5 inhibitors within the art, leading to the accumulation of cGMP. The inhibitors should at the same time have a very low or negligible effect on cAMP. High accumulation of cGMP and low effect on the levels of cAMP is a good indicator of the PDE5 inhibitor specificity.

SUMMARY OF THE INVENTION

Thus, the present invention relates to a compound having the general formula (I):

wherein

X is chosen from N and C;

$R_0$ is chosen from H, a lower alkyl group, a lower O-alkyl group, a lower aldehyde group, a benzyl group, a phenyl group, a phenyl group substituted with halogen or O-alkyl, a heterocyclic amine group, a cycloalkyl group, a cycloalkyl group substituted with O-alkyl, and a furyl group;

$R_1$ and $R_2$ are, independently, chosen from H, an amine group, a lower alkyl group, a lower O-alkyl group, a lower S-alkyl group and a lower N-alkyl group, or $R_1$ and $R_2$ taken together with the carbon atoms to which they are attached form a five-membered carbocyclic or heterocyclic ring, where the heteroatoms of the heterocyclic ring are chosen from O, S and N and/or where any substituent on said carbocyclic or heterocyclic ring is chosen from O, S and N;
n is 0, 1, 2, 3 or 4;
m is 0 or 1;
and pharmaceutically acceptable salts thereof;
with the proviso that said compound is not 1-[(4-methoxyphenyl)sulfonyl]piperazine or 1-(1,3-benzodioxol-5-yl-sulfonyl)piperazine.

The invention further relates to a compound according to above-mentioned formula (I) for use as a medicament.

Still further the invention relates to a pharmaceutical composition comprising a compound according to above-mentioned formula (I) as active ingredient together with a pharmaceutically acceptable adjuvant, diluent, excipient or carrier.

Yet further the invention relates to the use of a compound of the general formula (I)

(I)

wherein
X is chosen from N and C;
$R_0$ is chosen from H, a lower alkyl group, a lower O-alkyl group, a lower aldehyde group, a benzyl group, a phenyl group, a phenyl group substituted with halogen or O-alkyl, a heterocyclic amine group, a cycloalkyl group, a cycloalkyl group substituted with O-alkyl, and a furyl group;
$R_1$ and $R_2$ are, independently, chosen from H, an amine group, a lower alkyl group, a lower O-alkyl group, a lower S-alkyl group and a lower N-alkyl group, or $R_1$ and $R_2$ taken together with the carbon atoms to which they are attached form a five-membered carbocyclic or heterocyclic ring, where the heteroatoms of the heterocyclic ring are chosen from O, S and N and/or where any substituent on said carbocyclic or heterocyclic ring is chosen from O, S and N;
n is 0, 1, 2, 3 or 4;
m is 0 or 1;
and pharmaceutically acceptable salts thereof, as a selective PDE5-inhibitor for the manufacture of a medicament for the treatment of erectile dysfunction.

Still further the invention relates to a method for treatment of erectile dysfunction, comprising administering a therapeutically effective amount of a compound according to above-mentioned formula to an animal or human.

In one aspect of the invention, in the above mentioned formula, X is N, $R_o$ is chosen from H, methyl, methoxy and ethoxy and $R_1$ and $R_2$ are, independently, chosen from H, methyl, methoxy and ethoxy, or $R_1$ and $R_2$ taken together with the carbon atoms to which they are attached form a five-membered ring, wherein $R_1$ and $R_2$ are O.

In another aspect of the invention the compound of formula (I) is:

In the present disclosure the terms "lower" in "lower alkyl group", "lower O-alkyl group", "lower S-alkyl group", "lower N-alkyl group" and "lower aldehyde group" mean that the groups respectively comprise 1 to 6 carbon atoms, preferably 1 to 3 carbon atoms.

In the present disclosure a "heterocyclic amine group" is meant to be a heterocycle comprising from three to six atoms where at least one atom is a nitrogen and the remaining carbon atoms, said nitrogen being comprised within the heterocycle. Preferably the heterocycle comprise six atoms of which two are nitrogen atoms and the remaining carbon atoms. The expression "cycloalkyl group" in the present disclosure is meant a cyclic alkyl comprising from three to six carbon atoms.

In the present disclosure, unless otherwise indicated, lower alkyl group, lower O-alkyl group, lower S-alkyl and lower group N-alkyl group or any other entity comprising an alkyl group may be straight chain or branched chain. Halogen means fluoro, chloro, bromo or iodo, preferably fluoro and chloro.

In the present disclosure the atoms N, S and O in the groups "N-alkyl group", "S-alkyl group" and "O-alkyl group" may be attached to any possible entity of the group. An O-alkyl group of the present invention is typically a methoxy group or an ethoxy group and so on up to an O-alkyl group comprising 6 carbon atoms.

The pharmaceutical composition containing a compound of the present invention may be adapted for oral, intravenous, topical, intraperitoneal, nasal, buccal, sublingual or subcutaneous administration or for administration via the respiratory tract in the form of e.g. an aerosol or an air-suspended fine powder. Thus, the composition may be in the form of e.g. tablets, capsules, powders, micro-particles, granules, syrups, suspensions, solutions, transdermal patches or suppositories. Thus, the compounds of the present invention may be administered to a patient via any medically acceptable means of administration.

A pharmaceutically acceptable adjuvant, diluent, excipient or/and carrier may be associated with a compound of the present invention in a pharmaceutical composition. The different adjuvants, diluents, excepients and carriers that can be used together with a compound of the present invention in a pharmaceutical composition are well known to a person within the art. The adjuvants, diluents, excepients and carriers must be pharmaceutically acceptable in the sense of being compatible with the other ingredients of the pharmaceutical composition and not deleterious to the recipient thereof.

It should be noted that the pharmaceutical composition according to the present invention may optionally include two or more of the above outlined compounds. A compound of the present invention may also be administered in combination with other medicaments present within the art of erectile dysfunction or other related disorders. A compound of the present invention may for example be administered in combination with other PDE inhibitors useful within the art.

The typical dosage of the compounds according to the present invention varies within a wide range and will depend on various factors such as the individual requirement of each patient, the route of administration, the nature of the composition, the individuals body weight, age and general condition. The dosage is generally within the range of 0.01–100 mg/kg body weight for any of the different administration routes. Ultimately the dosage will be decided upon the discretion of the medical or veterinary practitioner.

The total daily dose may be given as a single dose or multiple doses. Dosages above or below the range cited above are within the scope of the present invention and may be administered to the individual patient if desired and necessary.

In the following detailed description of preferred embodiments of the invention the preparation of certain compounds of the invention is disclosed. The disclosure below should be construed as comprising the preparation of all compounds of the present invention.

DETAILED DESCRIPTION OF PREFERRED EMBODIMENTS OF THE INVENTION

The general synthetic pathway to the formula, wherein $R_1$ is O, C, S or N, and X is N or C, can be summarized as shown below:

The compounds (a) and (b) in the chemical synthesis above can have the following chemical structures.

TABLE 1

List of some of the chemical structures of compound (a)

| $R_1$ | Chemical Structures | Family |
|---|---|---|
| CH | | 2,3dihydrobenzofuranes |
| O | | 1,3-Benzodioxoles |
| S | | 1,3-Benzoxathiazoles |
| NH | | 1,3-Benzoxazoles |
| C=O | | 3-Benzofurones |
| C=S | | 3-Thioxobenzofurane |

TABLE 2

List of some of the chemical structures of compound (b) in the chemical synthesis, wherein $R_0$ is chosen from as defined above

| Y | Chemical Structure | Family |
|---|---|---|
| N | H—N⟨ ⟩N—$R_0$ | Piperazins |
| CH | H—N⟨ ⟩—$R_0$ | Piperadines |

A preferred compound according to the invention is:

, hereafter referred to as compound 1.

Preparation of Compound 1 of the Present Invention:

Step 1

(intermed. 1a)

1,3-Benzodioxole (3.0 g, 24.6 mmol) was diluted with ethylacetate (20 ml) and acetic anhydride (7.0 ml, 74 mmol) was charged. The solution was cooled using an ice water bath to a solution temperature of 3° C. after which sulfuric acid (1.5 ml, 26.7 mmol) was charged over 10 minutes. The ice-water bath was removed and the solution (slightly pink) was stirred at room temperature for 20 hours. HPLC revealed that >95% of the starting material was consumed after 1, 5 hours. Potassium-acetate (2.6 g, 26.7 mmol) dissolved in ethanol (10 ml, 95% (v/v) was charged to the solution over 20 minutes, controlling the exothermic reaction by cooling with an ice-water bath. The precipitated title compound (intermed. 1a) was stirred at 3° C. for an additional 15 minutes after which it was collected by suction filtration (glass filter, vacuum yielding 6.0 g (>100%). Mp>200° C. (dec.) $^1$H NMR (d6-DMSO): 7.15 (1H, d), 7.05 (1H, s), 6.81 (6.01 (2H, s)

Step 2

The compound from step 1 (intermed. 1a) (3.0 g, 12.5 mmol), dimethylformamide (3 drops), toluene (10 ml) and thionyl chloride (4.6 ml, 62.5 mmol) were mixed. The formed slurry was heated at 70° C. for 1 hour resulting in evolution of sulfurdioxide gas and dissolution of the formed title compound (intermediate 1b). The solvent was removed under reduced pressure and the residue was dissolved in toluene (30 ml). The toluene solution was extracted with water (30 ml), the water phase was separated off and the toluene solution was evaporated to dryness yielding an oil, which crystallized upon standing. M: 3.0 g (>100%), HPLC: 98-area % (254 nm)

TLC: rf 0,4 (homogeneous)

Step 3

1-methylpiperazine (1.4 ml, 12.5 mmol) and triethylamine (1.7 ml, 12.5 mmol) was diluted with methylenechloride (10 ml) and charged over 5 minutes to an ice-water cooled solution (approx. 2° C.) of intermed. 1b (12.5 mmol) dissolved in methylenechloride (10 ml). The slurry (Net3×HCl insoluble) was stirred at 3–4° C. for approximately 2 hours after which HPLC and TLC demonstrated full conversion. The organic solution was extracted twice with water (10 ml) and then evaporated to dryness. The solid residue (3.1 g) was recrystallized from hot methanol (15 ml), filtered off on a glass filter and dried under reduced pressure for 24 hours, yielding 1.9 g of the title compound (compound 1) as a white solid. Mp: 137–138° C. (corrected), HPLC (254 nm): "100 area %", HPLC (275 nm): >98.5 area %, $^1$H NMR (CDCl3):

FURTHER EXAMPLES OF PREPARED COMPOUNDS OF THE INVENTION

Example 1

Prepared Compound:

Transfer 61.5 ml of anisole (C₆H₅—O—CH₃) into a 250 ml round bottom flask and place the flask in an ice path. Add chlorsulfuric acid drop wise. After the addition is complete, stir for 3 hrs. Pour the content of the flask slowly and carefully over 400 gm ice in a 1 liter beaker. Filter under vacuum to collect a white precipitate. Dissolve the precipitate in CHCl₃ and dry with CaCl₂. Filter and then evaporate. Re-crystallize the residue using cyclohexane/petroleum ether to collect about 30 gm of a white solid (4-methoxybenzen sulfonylchloride).

Dissolve 5 gm 4-methoxybenzene sulfonylchloride in 40 ml CHCl₃ in 250 ml round bottom flask. Add 3.1 gm N-acetyl-piperazine and 6.8 ml triethylamine. Stir over night, then add 150 ml CHCl₃. Wash with 1 m HCl twice 150 ml each. Dry the organic layer using CaCO₃, filter, and then evaporate. Recrystallize the residue from ethylacetate/ether to collect about 5.48 gm. Dissolve 2 gm of the obtained material in 10 ml of 2M HCl in 100 ml round bottom flask. Reflux for 1.5 hours then allow cooling to room temperature. Pour the aqueous layer in a beaker and wash the round bottom flask with water. Basify the aqueous layer with Na₂CO₃ and place the basic solution in the fridge.

Example 2

Prepared Compound:

Transfer 61.5 ml of anisole into a 250 ml round bottom flask and place the flask on an ice bath. Add chlorosulfuric acid drop wise. After the addition is complete, stir the solution for 4 hours. Pour the content of the flask slowly and carefully over 400 gm of ice in a 1 liter beaker. Filter under vacuum to collect a white precipitate. Dissolve the precipitate in chloroform and dry with CaCl₂. Filter then evaporate. Re-crystallize the residue using cyclohexane/petroleum ether. Collect about 30 gm of a white solid (4-methoxybenzen sulfonylchloride). Dissolve 2 gm of 4-methoxybenzene sulfonylchloride in 40 ml chloroform in a 250 ml round bottom flask. Add 1,7 ml N-benzyl-piperazine, and 2,7 ml of triethylamine. Stir over night, then add 150 ml chloroform. Wash with (2M Na₂CO₃), filter, and then evaporate. Re-crystallize from ethylacetate/petroleum ether. Collect about 2.91 gm of the desired compound.

Example 3

Prepared Compound:

Dissolve 20 mmol of benzene sulfonylchloride in 20 ml tetrahydrofurane. Add the obtained solution to 20 mmol of N-methyl-piperazine in 20 ml tetrahydrofurane followed by the addition of 20 mmol triethylamine. Stir at room temperature for 2 hours. Evaporate under vacuum to get a powder or oily crude product. Triturate with ethanol and a few drops of water and cool. Collect by suction filtration and wash with water.

Example 4

Prepared Compound:

Dissolve 20 mmol of toluene sulfonylchloride in 20 ml tetrahydrofurane. Add the solution at room temperature to 20 mmol of N-methyl-piperazine in 20 ml tetrahydrofurane followed by 20 mmol triethylamine. Stir at room temperature for 2 hours. Evaporate under vacuum to get a powder or oily crude product. Triturate with ethanol and a few drops of water and cool. Collect by suction filtration and wash with water.

Example 5

Prepared Compound:

In minimum amount of water, dissolve N-propyl-piperazine and equivalent mmol of NaOH. Add equivalent mmol of benzene sulfonyl chloride. Control the temperature at 10° C. for 1 hour. Stir at room temperature over a period of 2 hours to get a precipitate. Collect the precipitate using suction filtration. Wash with water then cold ethanol:ether (1:1).

Example 6

Prepared Compound:

Make a solution of 20 mmol benzene sulfonylchloride in 20 ml tetrahydrofurane. Add this solution drop wise, with stirring at room temperature, to a solution of 20 mmol of N-4-methoxy-benzyl-piperazine in 20 ml tetrahydrofurane followed by 20 mmol triethylamine. The mix is stirred at room temperature for 2 hours. Evaporate under vacuum. Wash with 5 ml water twice. Wash with cold ethanol, then ether.

Example 7

Prepared Compound:

Make a solution of 20 mmol of benzene sulfonylchloride in 20 ml tetrahydrofurane. Add the solution drop wise under well stirring to a cold solution at 0° C. of 20 mmol of N-2-flouro-benzyl-piperazine in 20 ml tetrahydrofurane followed by 20 mmol triethylamine. Stir the mixture for 20 minutes at 0° C. then allow to raise to room temperature. Stir for 2 hours. Evaporate the solvent under vacuum. Wash the residue with water 5 ml (twice), cold EtOH then ether to get the crystalline product.

Example 8

Prepared Compound:

Make a solution of 20 mmol of toluene sulfonylchloride in 20 ml of tetrahydrofurane. Add this solution drop wise under vigorous stirring at room temperature to 20 mmol of N-4-methoxybenzyl piperazine in 20 ml of tetrahydrofurane, followed by triethylamine. Stir the mix for 2 hours at room temperature. Evaporate the solvent under vacuum. Wash the residue with 5 ml water twice. Wash with the cold ethanol and then ether.

Example 9

Prepared Compound:

In minimum amount of water dissolve an equivalent mmole of NaOH and N-2-tetrahydrofuranyl-piperazine. Add equivalent mmoles of 4-toluene sulfonylchloride. Control the temperature at 10° C. for 1 hour. Allow the mixture to stir at room temperature over a period of 2 hours to get a precipitate. Collect by suction filtration. Wash with cold water. Recrystallize from EtOH at room temperature.

Example 10

Prepared Compound:

In minimum amount of water dissolve equivalent mmol of NaOH and N-2-tetrahydro-furanyl-piperazine. Add equivalent mmoles of benzene sulfonylchloride. Control the temp. at 10° C. for 1 hour. Allow the mix to stir at room temperature over a period at 2 hours to get a precipitate. Filter by suction. Wash with cold water. Re-crystallize from EtOH at room temperature.

Example 11

Prepared Compound:

Place 61.5 ml of anisole in a 250 ml round bottom flask, place the flask in an ice bath. Add chlorosulfuric acid drop wise. After the addition is complete, stir the solution for 3 hours. Pour the content of the flask slowly and carefully over 400 gm of ice in a 1 liter beaker. Filter using vacuum filtration, to collect a white precipitate. Dissolve the precipitate in chloroform and dry with $CaCl_2$. Filter, then evaporate. Recrystallize the residue using cyclohexane/petroleumether, collect the white precipitate (about 30 gm) 4-methoxy benzene sulfonylchloride.

Dissolve 20 ml of 4-methoxybenzene sulfonylchloride in 40 ml chloroform in a 250 ml round bottom flask. Add 1.5 ml at 4-benzyl-piperdine and 2.7 ml triethylamine. Stir overnight, then add 150 ml $CHCl_3$. Wash with 1M HCl twice 150 ml each. Dry the organic layer with $CaCO_3$, filter and evaporate. Re-crystallize from ethylacetatet/petroleum ether.

Example 12

Prepared Compound:

Make a solution of 20 mmol of benzene sulfonyl chloride in 20 ml tetrahydrofuranyl followed by 20 mmol of triethylamine, under vigorous stirring at 0° C. Add the solution to 20 mmol of 4-methyl-1-amino piperazine, in 20 ml. Stir at 0° C. for 20 min, then allow to raise to room temperature and stir for 2 hours. Evaporate under vacuum. Wash the precipitate with 5 ml water twice, then with cold ethanol. Wash with ether to get the crystalline product.

Example 13

Prepared Compound:

Make a solution of 20 mmol of toluene sulfonylchloride in 20 ml of tetrahydrofuranyl. Add the solution drop wise under vigorous stirring and at 0° C. to 20 mmol of 4-methyl-1-amino-piperazine in 20 tetrahydrofuranyl, followed by 20 mmol of triethylamine. Stir for 20 mm at 0° C. then allow to raise to room temperature. Stir for 2 hours. Evaporate using vacuum, to get the precipitate. Wash with water 5 ml twice, then with cold ethanol. Wash with ether to get the crystallized white product.

Activity of the Compounds of the Invention

The purpose of the study was to compare the biological activity of compound 1 of the present invention with that of sildenafil. In particular, the respective $ED_{50}$ value (ED=effective dose), erection episodes and penile erection indexes of said compounds in the treatment of male rats were determined. The penile erection index is an established means of determining the erection promoting properties of a substance (see e.g. Benassi-Benelli, F., Ferari, F., and Pellegrini Quaratotti, B., Arch. Int. Pharmacodyn., 242, 241–247, (1979), and Ang. H. H., Sim, M. K., Pharm. Sci., 3, 17–119, (1997) and references cited therein).

In these experiments, compound 1 of the present invention and sildenafil were administered to male rats orally. The doses for sildenafil were 0.0781, 0.1562, 0.3125 and 0.625 mg/kg body weight, while doses for compound 1 of the present invention were 0.3, 0.6, 1, and 2 mg/kg body weight. Both sildenafil and compound 1 of the present invention were dissolved in distilled water. Control animals were administered with water. During the experiments, the rats were placed in glass cages for observation and had free access to food and water. During 2 hours after administration of the investigated compound, the penile erection and self-sucking were monitored. It is worth mentioning that no copulation mounting behavior was observed in these experiments. The number of rats responding to this experiment protocol was recorded, and the $ED_{50}$ results are shown in Table 3.

TABLE 3

Study of number and percentage of responses as a function of dose for rats subjected to sildenafil Table (3A) and compound 1 of the present invention Table (3B), respectively.

Table (3A)

| Dose[1] (mg/kg) | No. Rats used | Sildenafil responding rats[2] | | |
|---|---|---|---|---|
| | | No. | % | PEI |
| 0.0781 | 10 | 3 | 30 | 90 |
| 0.1562 | 10 | 5 | 30 | 150 |
| 0.3125 | 10 | 7 | 50 | 350 |
| 0.625 | 10 | 14 | 70 | 980 |

Table (3B)

| Dose[1] (mg/kg) | No. Rats used | Compound 1 responding rats[3] | | |
|---|---|---|---|---|
| | | No. | % | PEI |
| 0.3 | 10 | 1.5 | 15 | 22.5 |
| 0.6 | 10 | 6.5 | 40 | 260 |
| 1.0 | 10 | 9.5 | 70 | 665 |
| 2.0 | 10 | 12 | 85 | 1020 |

[1]No rats responded when distilled waster was administered
[2]Calculated $ED_{50}$ = 0.2473 mg/kg body weight
[3]Calculated $ED_{50}$ = 0.7822 mg/kg body weight

EXAMPLES OF COMPOUNDS OF THE PRESENT INVENTION AND THE PEI FOR SELECTED MOLECULES

TABLE 4

List of some derivatives of the compound of the present invention with the PEI (penile erection indexes) for selected molecules.

(where X is N or CH)
In Table (4) below X = N.

| —$R_0$ | —$R_1$ | PEI |
|---|---|---|
| —H | —$OCH_3$ | 1800 |
| —$OCH_3$ | —$OCH_3$ | — |
| | —$OCH_3$ | — |
| —$CH_2$—phenyl | —$OCH_3$ | — |
| phenyl | —H | 420 |
| —$CH_3$ | —$CH_3$ | 240 |
| —$CH_3$ | —$NH_2$ | — |
| phenyl | —$NH_2$ | — |
| —$CH_3$ | —$NH_2$ | — |

TABLE 4-continued

List of some derivatives of the compound of the present invention with the PEI (penile erection indexes) for selected molecules.

(where X is N or CH)
In Table (4) below X = N.

| —R₀ | —R₁ | PEI |
|---|---|---|
| —CH₂-phenyl | —NH₂ | — |
| 2-(1,3-diazinan-2-yl) | —NH₂ | — |
| —CH₂CH₂CH₃ | —H | — |
| 4-methoxyphenyl | —H | — |
| 4-ethoxycyclohexyl | —H | — |
| 2-methylphenyl | —H | — |
| 2-methylphenyl | —CH₃ | — |
| 4-fluorophenyl | —H | — |
| 4-chlorophenyl | —H | — |
| (unspecified) | —CH₃ | — |
| 4-methoxyphenyl | —CH₃ | — |
| 2-furyl | —CH₃ | — |
| 2-furyl | —H | — |
| —CHO | —H | — |
| —CHO | —CH₃ | — |
| 4-ethoxyphenyl | —CH₃ | — |
| —H | —OCH₂CH₃ | — |
| —OCH₂CH₃ | —OCH₂CH₃ | — |
| —CH₂-phenyl | —OCH₂CH₃ | — |
| 3-methylphenyl | —OCH₂CH₃ | — |

TABLE 4-continued

List of some derivatives of the compound of the present invention with the PEI (penile erection indexes) for selected molecules.

(where X is N or CH)
In Table (4) below X = N.

| —R₀ | —R₁ | PEI |
|---|---|---|
| —CH₂-phenyl | —NH₂ | — |
| —CH₂-phenyl | —OCH₃ | — |

TABLE 5

List of further compounds of the present invention with the PEI (penile erection indexes) for selected molecules.

(wherein X is N or CH)
In Table (5) below X = N.

| R₀ | R₁ | R₂ | PEI |
|---|---|---|---|
| —CH₃ | O | O | — |
| —CH₃ | O | O | — |
| 2-(1,3-diazinan-2-yl) | | | |
| phenyl | O | O | — |
| —CH₂-phenyl | O | O | — |
| 2-(1,3-diazinan-2-yl) | O | O | — |
| —CH₂-phenyl | | | |
| —CH₃ | O | O | 1015 |
| —H | O | O | — |
| —H | O | C | — |

TABLE 6

List of further compounds of the present invention with the PEI (penile erection indexes) for selected molecules.

In Table (6) below X = N.

| $R_0$ | $R_1$ | n | PEI |
|---|---|---|---|
| —$CH_3$ | —H | 0 | 80 |
| —$CH_3$ | —$CH_3$ | 0 | 90 |
| —H | —$OCH_2CH_3$ | 0 | — |
| —H | —$OCH_3$ | 0 | — |
| —H | —$OCH_2CH_3$ | 1,2,3,4 | — |
| —H | —$OCH_3$ | 1,2,3,4 | — |
| —H | —H | 1,2,3,4 | — |
| —$CH_3$ | —$OCH_3$ | 0 | — |
| —$CH_3$ | —$OCH_2CH_3$ | 0 | — |

Method for Analysis of cGMP & cAMP Synthesis and Accumulation in Penile Tissues:

White New Zealand rabbits were sacrificed. Excise the penises rapidly after killing the animals, remove epidermal & connective tissue. Dissect out and discard the urethra carefully. Cut the penises longitudinally into 2 equal strips and then laterally to give about 20–40 segments. Pool and incubate the segments of the corpus cavernosum in Dulbecco's minimum essential Medium (MEM) at room temperature for one hour to allow the tissues to recover from preparative handling.

Effect of Drug on cGMP and cAMP Formation:

Place one penile segment in triplicate for each drug dose in 200 µl MEM. Place one penile segment in triplicate for each drug dose with 10 µM SNP (sodium nitroprusside) in 200 µl MEM. (in the case of cGMP). Incubate the tubes at 37° C. for 30 min, stop the reaction by adding 200 µl of 1 mol/l perchloric acid and sonicate for 5 min. Neutralize the aliquots with 0.5 mol/l $K_3PO_4.3H_2O$ to pH 6.2 (240 µl), centrifuge and take the supernatant in aliquots. Keep at 4° C. and assay for the concentrations of cAMP and cGMP in the extract using ELISA (enzyme linked immunosorbant assay). Preparation of Zero sample: Add 200 ul MEM, 200 ul 1M perchloric acid and 240 µl 0.5 mol/L $K_3PO_4.3H_2O$ in one tube.

Drug Solutions—Preparation of MEM Containing Sildenafil Citrate and Compound 1

The main concentrations were in the range 0–20,000 or 100,000 nM. A stock solution of 1 mM for both drugs were prepared in distilled water. Serial dilution were prepared in MEM giving working drug concentrations of 0, 1000, 4000, 8000, 10000, 20000 and 100000 nM. In the case of cGMP the tests were carried out with and without NO donor (SNP). For this purpose 10 µM SNP was included when necessary.

RESULTS

Figure 1:
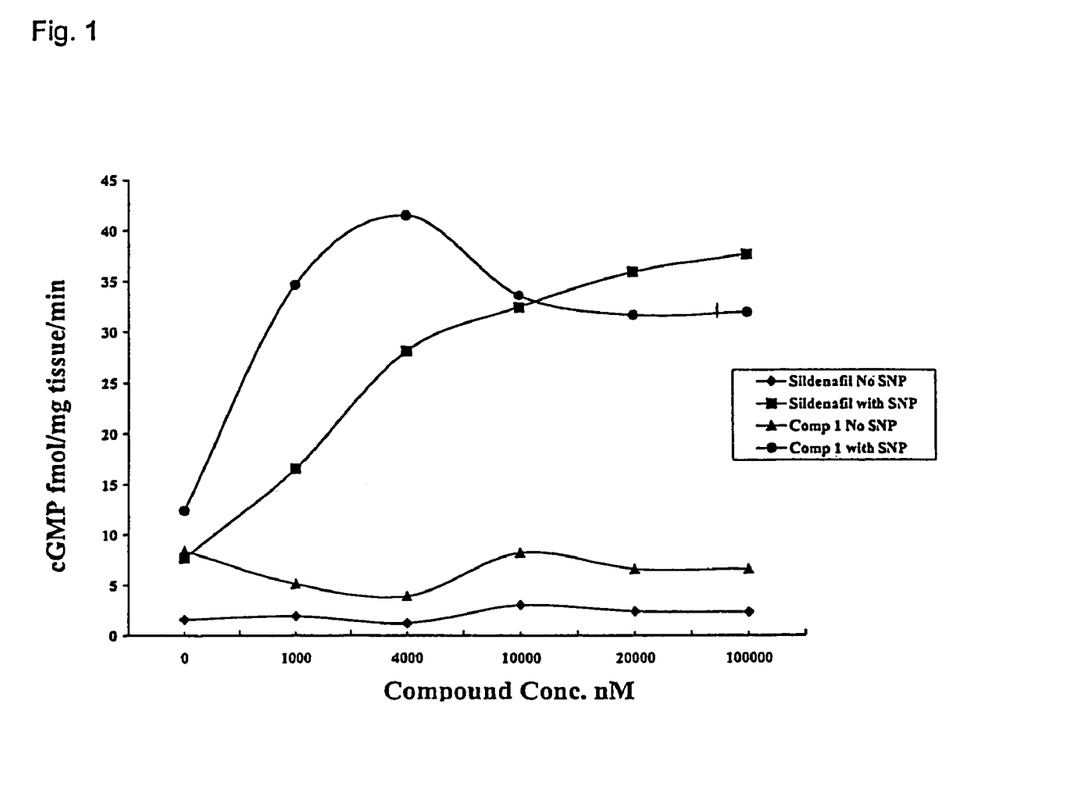
FIG. 1 shows the effect of sildenafil and compound 1 of the present invention on the accumulation of cGMP in isolated rabbit corpus carvenosum tissue. Since the accumulation of cGMP is NO dependent, accumulation was determined in the presence and absence of nitrogen donor.

In FIG. 1 it can be seen that both sildenafil and compound 1 of the present invention have very little effect on the levels of cGMP over the tested concentrations up to 100,000 nM. When NO donor was added, very strong response on cGMP accumulation was noticed. Sildenafil increased levels of cGMP giving a maximum increase at about 10,000 nM. Compound 1 showed a better response giving a maximum increase at about 4000 nM. Additionally, compound 1 of the present invention had a better effect than sildenafil at 10,000 nM. This will indicate or suggest a better affinity and potency of compound 1 of the present invention over sildenafil in inhibiting PDE5 type enzyme in the corpus carvenosum. Also worth pointing out is that compound 1 has a weak effect on the levels of CGMP in the absence of NO donor compared to an almost flat effect for sildenafil. This again lends more evidence and support for the more specificity and affinity of compound 1 of the present invention towards the inhibition of PDE5, in comparison to sildenafil.

Figure 2:
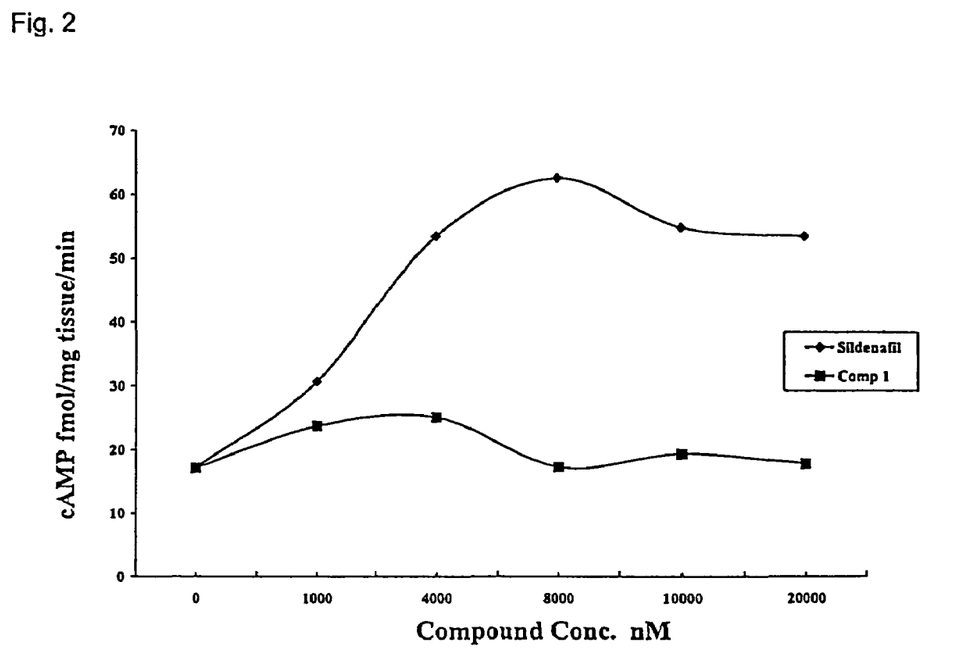
FIG. 2 shows the effect of sildenafil and compound 1 of the present invention on the accumulation of cAMP in the same tissue.

In FIG. 2 comparison was done on the effect of both compounds sildenafil and compound 1 on the accumulation of cAMP levels in the absence of NO donor. It is very interesting to note that compound 1 has no effect at all in increasing the intrinsic levels of cAMP in the tissue up to 20,000 nM. Sildenafil showed a remarkable increase in cAMP levels with a maximum increase obtained between 8000–10,000 nM. This strongly suggest that sildenafil has an inhibitory effect on a cAMP degrading PDE in the corpora carvenosum (could be PDE2, PDE3, PDE4 and possibly PDE1), thus accumulating cAMP. This effect was more profound and effective at high concentrations. Compound 1 of the present invention did not show such an effect, suggesting it has no inhibitory effect towards cAMP system, thus being more specific of cGMP.

We can conclude from the above experiments that a compound of the present invention is a better, more specific, more potent inhibitor for PDE5 cGMP specific type enzymes than sildenafil. This will definitely lead to a lesser dose of the active compound in the medicament needed for the treatment of erectile dysfunction, leading to reduced toxic side effects.

The invention claimed is:

1. A compound having the general formula (I):

wherein

X is N;

$R_0$ is H, a lower alkyl group, a lower O-alkyl group, lower alkyl group,
a benzyl group, a phenyl group, a phenyl group substituted with halogen or O-alkyl, a saturated heterocyclic amine group having two nitrogen atoms, a cycloalkyl group, a cycloalkyl group substituted with O-alkyl, and a furyl group;

$R_1$ and $R_2$ taken together with the carbon atoms to which they are attached form an unsubstituted five-membered heterocyclic ring, where the heteroatoms of the heterocyclic ring are one or two oxygen atoms;

n is 0, 1, 2, 3 or 4;

m is 0 or 1;

and pharmaceutically acceptable salts thereof;

with the proviso that said compound is not 1-(1,3-benzodioxol-5-ylsulfonyl)piperazine.

2. A compound according to claim 1, wherein $R_0$ is H, methyl, methoxy or ethoxy.

3. A compound according to claim 1, wherein $R_1$ and $R_2$ taken together with the carbon atoms to which they are attached form an unsubstituted five-membered heterocyclic ring that has two oxygen atoms.

4. A compound according to claim 1, wherein said compound is:

5. A pharmaceutical composition comprising a compound according to claim 1 or 4 as an active ingredient together with a pharmaceutically acceptable adjuvant, diluent, excepient or carrier.

6. A method for treatment of erectile dysfunction, comprising administering to an animal or human suffering from erectile dysfunction a therapeutically effective amount of a compound according to claim 1.

* * * * *